(12) United States Patent
Spaulding et al.

(10) Patent No.: US 9,067,085 B2
(45) Date of Patent: Jun. 30, 2015

(54) ENHANCED PHOTOCONDUCTIVITY AND SPF OF SEMICONDUCTORS

(75) Inventors: Laura A. Spaulding, Allendale, NJ (US); A. Christopher Pattillo, Allendale, NJ (US); Patricia L. Scott, Allendale, NJ (US)

(73) Assignee: Eveready Battery Company, Inc, St. Louis, MO (US)

( * ) Notice: Subject to any disclaimer, the term of this patent is extended or adjusted under 35 U.S.C. 154(b) by 545 days.

(21) Appl. No.: 12/483,943

(22) Filed: Jun. 12, 2009

(65) Prior Publication Data

US 2009/0311207 A1    Dec. 17, 2009

Related U.S. Application Data

(60) Provisional application No. 61/131,982, filed on Jun. 13, 2008.

(51) Int. Cl.

| | |
|---|---|
| *A61K 8/72* | (2006.01) |
| *C08K 3/22* | (2006.01) |
| *C08L 53/00* | (2006.01) |
| *C08K 5/101* | (2006.01) |
| *A61Q 17/04* | (2006.01) |
| *A61K 8/27* | (2006.01) |
| *A61K 8/29* | (2006.01) |
| *A61K 8/81* | (2006.01) |
| *A61K 8/90* | (2006.01) |
| *C08L 53/02* | (2006.01) |
| *C09C 1/36* | (2006.01) |
| *C09C 1/04* | (2006.01) |
| *C08L 25/18* | (2006.01) |

(52) U.S. Cl.
CPC . *A61Q 17/04* (2013.01); *A61K 8/27* (2013.01); *A61K 8/29* (2013.01); *A61K 8/8117* (2013.01); *A61K 8/90* (2013.01); *C08K 3/22* (2013.01); *C08L 25/18* (2013.01); *C08L 53/025* (2013.01); *C09C 1/3676* (2013.01); *C09C 1/043* (2013.01); *C01P 2004/61* (2013.01)

(58) Field of Classification Search
None
See application file for complete search history.

(56) References Cited

U.S. PATENT DOCUMENTS

| | | |
|---|---|---|
| 5,587,148 A | 12/1996 | Mitchell et al. |
| 5,618,522 A | 4/1997 | Kaleta |
| 5,776,440 A | 7/1998 | Forestier |
| 5,939,053 A | 8/1999 | Forestier |
| 6,060,041 A | 5/2000 | Candau |
| 6,235,271 B1 | 5/2001 | Luther |
| 6,361,782 B1 | 3/2002 | Chevalier et al. |
| 6,440,402 B1 | 8/2002 | Gonzalez |
| 6,444,647 B1 | 9/2002 | Robinson |
| 6,492,326 B1 | 12/2002 | Robinson |
| 6,500,411 B2 | 12/2002 | SenGupta |
| 6,716,418 B2 | 4/2004 | SenGupta |
| 6,881,776 B2 | 4/2005 | Butuc |
| 7,098,189 B2 | 8/2006 | Malik |
| 7,108,860 B2 | 9/2006 | Dueva |
| 7,276,230 B2 | 10/2007 | Gonzalez |
| 2004/0009130 A1* | 1/2004 | Detore et al. ................... 424/59 |
| 2004/0048836 A1* | 3/2004 | Wilmott ........................ 514/159 |
| 2005/0004274 A1* | 1/2005 | Healy et al. ..................... 524/80 |
| 2005/0013781 A1 | 1/2005 | Dueva-Koganov |
| 2007/0006802 A1 | 1/2007 | Nause |
| 2007/0196295 A1 | 8/2007 | Cantwell et al. |
| 2008/0112904 A1 | 5/2008 | Traynor et al. |
| 2009/0057627 A1 | 3/2009 | Bonda et al. |
| 2009/0186055 A1 | 7/2009 | Dumousseaux et al. |

OTHER PUBLICATIONS

International Search Report and Written Opinion from PCT/US2009/03526 dated Aug. 11, 2009.
Definition of Photoconductivity from Wikipedia (http://en.wikipedia.org/wiki/Photoconductivity).
Definition of Semiconductor from Wikipedia (http://en.wikipedia.org/wiki/Semiconductor).
Definition of Bandgap from Wikipedia (http://en.wikipedia.org/wiki/Bandgap).
List of Semiconductor Materials from Wikipedia (http://en.wikipedia.org/wiki/List_of-semiconductor_materials.
International Preliminary Report on Patentability from PCT/US2009/03526 dated Feb. 18, 2011.
International Search Report and Written Opinion from PCT/US2010/49106 dated Nov. 1, 2010.
Kraton G 1650 M Polymer Data Document.

* cited by examiner

*Primary Examiner* — Mina Haghighatian
*Assistant Examiner* — Luke Karpinski
(74) *Attorney, Agent, or Firm* — Energizer Personal Care, LLC.

(57) ABSTRACT

The present disclosure provides a way to enhance the photoconductivity and/or the SPF of a semiconductor. By dispersing the semiconductor with a compound having multiple phenyl groups in a polar carrier oil, the semiconductor exhibits greatly improved photoconductivity and/or SPF over dispersions comprising the semiconductor alone.

14 Claims, 11 Drawing Sheets

ENHANCED PHOTOCONDUCTIVITY AND SPF OF SEMICONDUCTORS

CROSS-REFERENCE TO RELATED APPLICATIONS

The present application claims the benefit of U.S. Provisional Application No. 61/131,982, filed on Jun. 13, 2008.

BACKGROUND OF THE DISCLOSURE

1. Field of the Disclosure

The present disclosure relates to enhancing the photoconductivity and/or sun protection factor (SPF) of semiconductors. In particular, the present disclosure relates to enhancing these properties of semiconductors by dispersing them with chemical compounds having multiple phenyl groups, in a polar organic carrier oil.

2. Description of the Related Art

Photoconductivity of a semiconductor refers to the material's ability to become more conductive when exposed to light. Enhancing the photoconductivity of the semiconductor can thus improve its performance in a variety of electronic applications. Some semiconductors are also useful as sunscreen active agents. It is always a goal in the field of suncare to either use less sunscreen active material while maintaining a desired level of SPF, or to achieve a very high SPF overall. Thus, there is a need to a way of enhancing the photoconductivity and/or the SPF of semiconductor materials.

SUMMARY OF THE DISCLOSURE

The present disclosure thus provides dispersions and compositions that enhance the photoconductivity and/or the SPF of semiconductors.

In one embodiment, the present disclosure provides a dispersion comprising a semiconductor, a compound having multiple phenyl groups, and a polar carrier oil.

In another embodiment, the present disclosure provides a sunscreen composition, comprising a sunscreen and a dispersion. The dispersion comprises a semiconductor, a compound having multiple phenyl groups, and a polar carrier oil.

DETAILED DESCRIPTION OF THE DISCLOSURE

Figure 1:
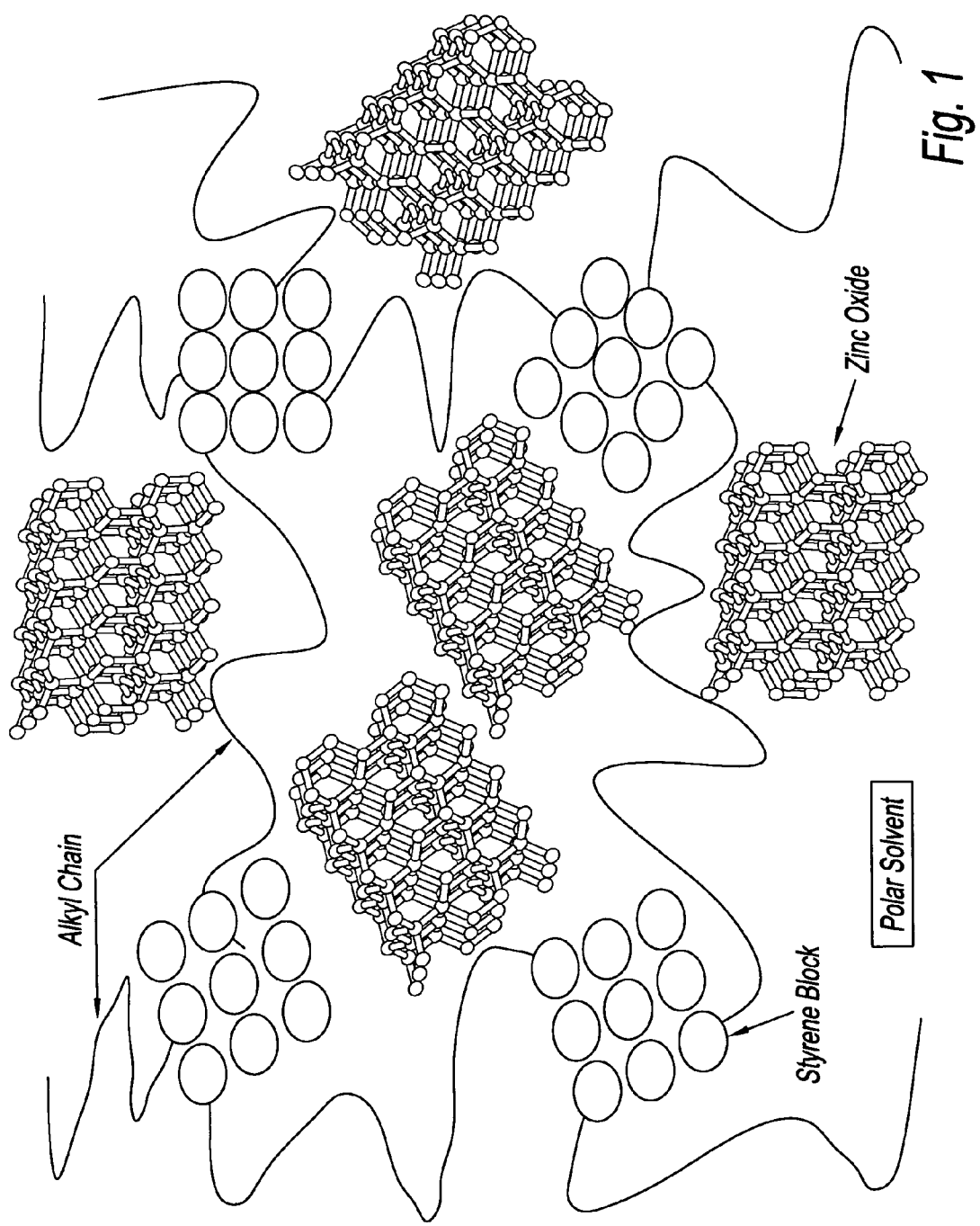
FIG. 1 is a conceptual drawing of a dispersion of the present disclosure.

The present disclosure has unexpectedly discovered that when a semiconductor, such as zinc oxide or titanium dioxide, is combined with compounds containing multiple (i.e., at least two) phenyl groups, the photoconductivity and the SPF of the semiconductor are significantly enhanced. This is contrary to the common understanding of how to boost these characteristics. Previously, it was thought that to enhance photoconductivity or SPF, dopants would have to be added to the crystal lattice structure of the semiconductor. The present disclosure, by contrast, has discovered that the photoconductivity and SPF can be increased by combining the semiconductor, with the aforementioned compounds having multiple phenyl groups (hereinafter "phenyl compounds"), in a dispersion. Thus, the photoconductivity and SPF of a semiconductor can be enhanced without undergoing complicated and costly doping processes. This results in less semiconductor material being required for a particular application, or in dispersions and compositions having high SPF values that were previously not thought possible.

The present disclosure thus provides a dispersion comprising a semiconductor, a phenyl compound, and a polar carrier oil as a solvent. In one embodiment, the semiconductor can be one or more semiconductors selected from the group recited in the Wikipedia page, "List of semiconductor materials," found at http://en.wikipedia.org/wiki/List_of_semiconductor_materials, which is herein incorporated by reference. In another embodiment, the semiconductor is selected from the group consisting of titanium dioxide, zinc oxide, which can double as sunscreen actives, and a combination thereof. The semiconductor can be present in an amount of about 0.50 wt % to about 35.00 wt %, or about 20.00 wt % to about 30.00 wt %, based on the total weight of the dispersion. The semiconductor can also be present in precisely those amounts, i.e. 0.50 wt % to 35.00 wt %, or 20.00 wt % to 30.00 wt %, based on the total weight of the dispersion. When present, the zinc oxide used in the present disclosure can be acquired from a number of vendors, such as Advanced Nanotech, the Umicore Group, or BASF.

In one embodiment, the phenyl compound can be selected from the group consisting of sodium polystyrene benzene sulfonate (available as Flexan® II, from AzkoNobel), an ethylene/butadiene/styrene block copolymer (available as Kraton® 1650, from Kraton Polymers), and combinations thereof. The phenyl compound can be present in an amount of about 0.05 wt % to about 10.00 wt %, or about 0.10 wt % to about 5 wt %, based on the total weight of the dispersion. The phenyl compound can also be present in precisely those amounts, i.e. 0.05 wt % to 10.00 wt %, or 0.10 wt % to 5 wt %, based on the total weight of the dispersion.

The polar carrier oil can be any oil that is suitable for the purpose of allowing the phenyl compounds to interact with the semiconductors in the manner discussed below. In one embodiment, the polar carrier oil can be selected from the group consisting of isopropyl myristate, butyloctyl salicylate, octisalate, isononyl isonanoate, and ethylhexyl benzoate, or any combinations thereof. The polar carrier oil can be present in an amount of about 65.00 wt % to about 99.50 wt %, or about 75.00 wt % to about 95.00 wt %, based on the total weight of the dispersion. The polar carrier oil can also be present in precisely those amounts, i.e. 65.00 wt % to 99.50 wt %, or 75.00 wt % to 95.00 wt %, based on the total weight of the dispersion.

Without being bound by a specific theory, it is believed that the phenyl compound causes a large electronegative cloud to come into contact with the surface of the semiconductor, thus causing an increase in the photoconductivity and/or SPF of the semiconductor. Traditionally, semiconductors are often doped in an attempt to help the electrons residing in the valence bands of the semiconductor material cross the band gap to the conduction bands when the semiconductor is exposed to light, which enhances the conductivity of the semiconductor. The dopant donates valence electrons, thus making the migration across the band gap easier.

In the dispersions of the present disclosure, however, there is no need to dope the semiconductor. The phenyl compounds act as external dopants to the semiconductor, as opposed to traditional dopants (sometimes referred to as "extrinsic" dopants), which would be located within the semiconductor crystal lattice. The large electronegative cloud provided by the phenyl compound can facilitate the "jump" of valence electrons to the conduction bands, in part because in some semiconductors, there are no electron orbitals in the band gap region. Also, this relatively large, strong electronegative cloud has the ability to polarize the filled d-orbitals of some semiconductors, thus distorting the orbitals and ultimately affecting the band gap region, thereby facilitating electron flow. It is possible that the phenyl compounds may be acting as n-type dopants (donating electrons) to produce the n-type semiconductor. A conceptual drawing of this concept is shown in FIG. 1.

There are many useful applications for the dispersions of the present disclosure, due to their enhanced photoconductivity and SPF characteristics. For example, such a dispersion would be extremely valuable in any number of electronics applications, such as in computing devices, cellular phones, batteries, optoelectronic devices, photovoltaic cells, and others. The enhanced SPF of this dispersion is particularly valuable in the field of personal care and sunscreen compositions.

To observe the effects that the dispersions of the present disclosure can have on the SPF of a semiconductor, several different dispersions were tested, as shown in Table 1 below. The dispersions were all applied at a coverage rate in the amounts described below, and analyzed with a Labsphere 1000S UV Transmittance Analyzer for SPF value.

TABLE 1

| Composition | SPF |
|---|---|
| Isopropyl Myristate (IPM)(Control) | 0.73 |
| 10% Kraton 1650 in IPM | 0.73 |
| Zinc Oxide (ZnO) at 0.2332 mg/cm$^2$ in IPM | 8.63 |
| ZnO at 0.2332 mg/cm$^2$ + Kraton 1650 at 0.0932 mg/cm$^2$ + 10% Kraton 1650 in IPM | 28.95 |

Thus, as shown above, the Kraton 1650 polymer greatly enhances the SPF of zinc oxide, when in a dispersion with IPM. This is a very unexpected result. It was not thought possible to enhance the SPF of a semiconductor, such as zinc oxide, with the use of a phenyl compound, such as Kraton 1650, because as shown above, the latter has no SPF value on its own. Yet, when the Kraton 1650 is added to the zinc oxide, the resulting dispersion has a greatly enhanced SPF value when compared to a dispersion having zinc oxide alone. The dispersions discussed in the present disclosure can thus be used in sunscreen formulations, where they will provide significantly enhanced SPF characteristics. The resultant sunscreen formulations can have high SPF and UVA/UVB absorption values, while only requiring smaller amounts of the semiconductor materials in the formulation. Alternatively, the dispersions of the present disclosure can be used to create compositions having high SPF values that were not previously thought possible.

The dispersions of the present disclosure can be used alone, or combined into a sunscreen composition with one or more additional sunscreen actives other than the semiconductors which also function as sunscreen actives. The one or more additional sunscreen actives can be, but are not limited to, cinnamates, homosalate, octisalate, oxybenzone, avobenzone, and octocrylene, and can be present in an amount of about 3 wt % to about 12 wt % of the composition, or in precisely these amounts, i.e. 3 wt % to 12 wt % of the composition. The composition may also comprise one or more additives, such as emulsifiers, thickeners, emollients, pH adjusters, stabilizers, and film formers. The dispersion can be present in the sunscreen composition so that the amount of semiconductor present in the sunscreen composition is between about 1.00 wt % and about 5.00 wt %, or in precisely these amounts, i.e. between 1.00 wt % and 5 wt %.

The following data further illustrates the advantages of the dispersions of the present disclosure.
Materials Used
ZnO Powder 45 nm and 75 nm Particle Size
Ethylhexyl salicylate (OS), butyloctyl salicylate (BHB), ethylhexyl benzoate (EB),
isopropyl myristate (IPM), and isononyl isonanoate (II)
Dispersions:
5% Kraton G1650 (K, Kraton) in Isopropyl Myristate (IPM)
5% Kraton G1650 (K, Kraton) in Ethylhexyl Benzoate (EB)
5% Kraton G1650 (K, Kraton) in Butyloctyl Salicylate (BHB)
5% Kraton G1650 (K, Kraton) in Ethylhexyl Salicylate (OS)

| | |
|---|---|
| ZnO (IPM) | 20% ZnO in Isopropyl Myristate |
| ZnO (II) | 20% ZnO in Isononyl Isonanoate |
| ZnO (EB) | 20% ZnO in Ethylhexyl Benzoate |
| ZnO (K EB) | 20% ZnO in 5% Kraton G1650/Ethylhexyl Benzoate Blend |
| ZnO (BHB) | 20% ZnO in Butyloctyl Salicylate |
| ZnO (K BHB) | 20% ZnO in 5% Kraton G1650/Butyloctyl Salicylate Blend |
| ZnO (OS) | 20% ZnO in Octisalate (Ethylhexyl Salicylate) |
| ZnO (K OS) | 20% ZnO in 5% Kraton G1650/Octisalate Blend |

For the ZnO dispersions, a Ross homogenizer was utilized to break-up the ZnO aggregates to help maximize content uniformity within and among the sample dispersions.
Results from SPF Studies The in-vitro SPF results summarized in Table II demonstrate the effect of solvent polarity on ZnO, and surprisingly, the substantial boost in SPF from the combination of the solvent and Kraton polymer.

TABLE II

Effect of ZnO (45 nm)/Kraton/Solvent on In-Vitro SPF

| | SPF (units) | | | | |
|---|---|---|---|---|---|
| Sample | IPM | II | EB | BHB | OS |
| Neat | 0.99 | 0.99 | 1.04 | 15.05 | 16.03 |
| +Kraton | 1.02 | 0.97 | 1.00 | 14.82 | 15.37 |
| +ZnO | 6.84 | 14.37 | 21.58 | 78.88 | 72.80 |
| +Kraton + ZnO | 62.46 | 55.11 | 66.16 | 123.48 | 133.04 |

Kraton polymer is a solid material that must be dispersed in solvent. The data in Table II suggests that the Kraton polymer not only has no SPF value on its own, but may actually slightly depress the SPF of the polar solvent. The dielectric constant for the Kraton/BHB and Kraton/OS blends without the presence of ZnO are 5.21 and 5.98, respectively, as shown in Table V below. Therefore, the dielectric constant data supports the slightly lower SPF trend noted for adding the Kraton polymer to the polar solvent.

Although ZnO in the Kraton/solvent blends does increase the SPF, it is the significance of the increase produced by the combination of the ZnO lattice structure in close proximity to the Kraton web-like matrix that becomes important. For the combination of ZnO/Kraton/BHB and ZnO/Kraton/OS dispersions, there was a remarkable 8.33 and 8.66 fold increase in SPF response versus the corresponding Kraton/solvent blend. Additionally, the combination of ZnO/Kraton versus ZnO alone showed a remarkable SPF unit increase by 56.5% in BHB, and 82.7% increase in OS solvents.

The data presented in Table III below demonstrates that the increase in observed SPF for the ZnO/Kraton/polar solvent dispersions were unexpectedly synergistic and not just additive. The Theoretical SPF is the sum of the SPF values for the dispersions for the Kraton and ZnO individually. So, for example, with the IPM dispersion, the Theoretical SPF would be 1.02+6.84=7.86, based on the values from Table III above. However, SPF values increased 30-55 units above what would normally be expected from an additive effect. The synergistic SPF effect was +31.8% for ZnO/Kraton in BHB, and +50.9% for ZnO/Kraton in OS. Hence, the photoconductivity of ZnO is synergistically enhanced by the combination of Kraton and polar solvent.

TABLE III

Determination of Additive versus Synergistic Effect for In-Vitro SPF with ZnO

| | SPF (units) | | | | |
|---|---|---|---|---|---|
| Sample | IPM | II | EB | BHB | OS |
| Theoretical SPF Solvent + Kraton + ZnO | 7.86 | 15.34 | 22.58 | 93.70 | 88.17 |
| Observed SPF Solvent + Kraton + ZnO | 62.46 | 55.11 | 66.16 | 123.48 | 133.04 |
| SPF Unit Difference | +54.60 | +39.77 | +43.31 | +29.78 | +44.87 |

Figure 2:
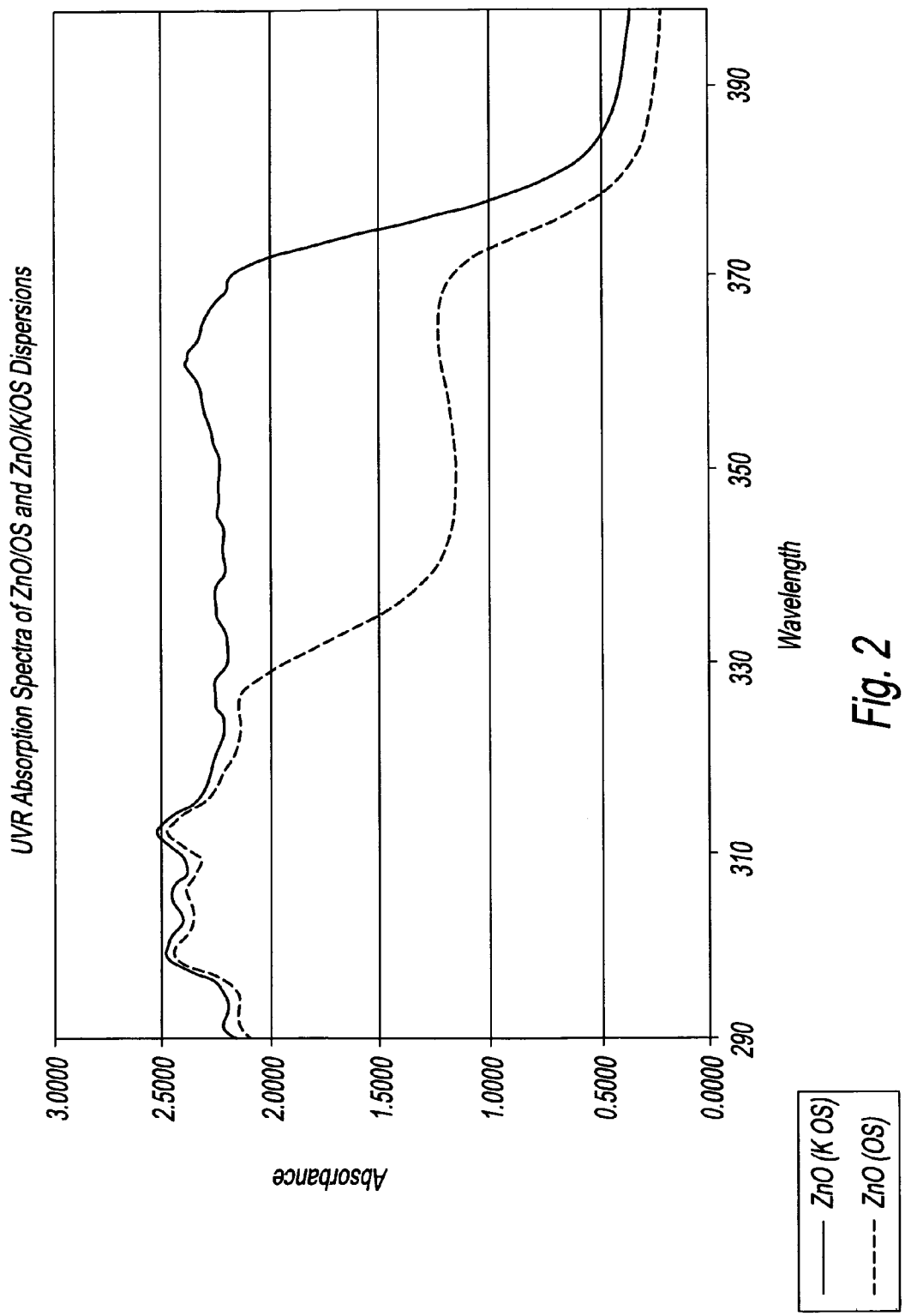
FIGS. 2-4 show UV absorption data for several dispersions of the present disclosure.
Figure 3:
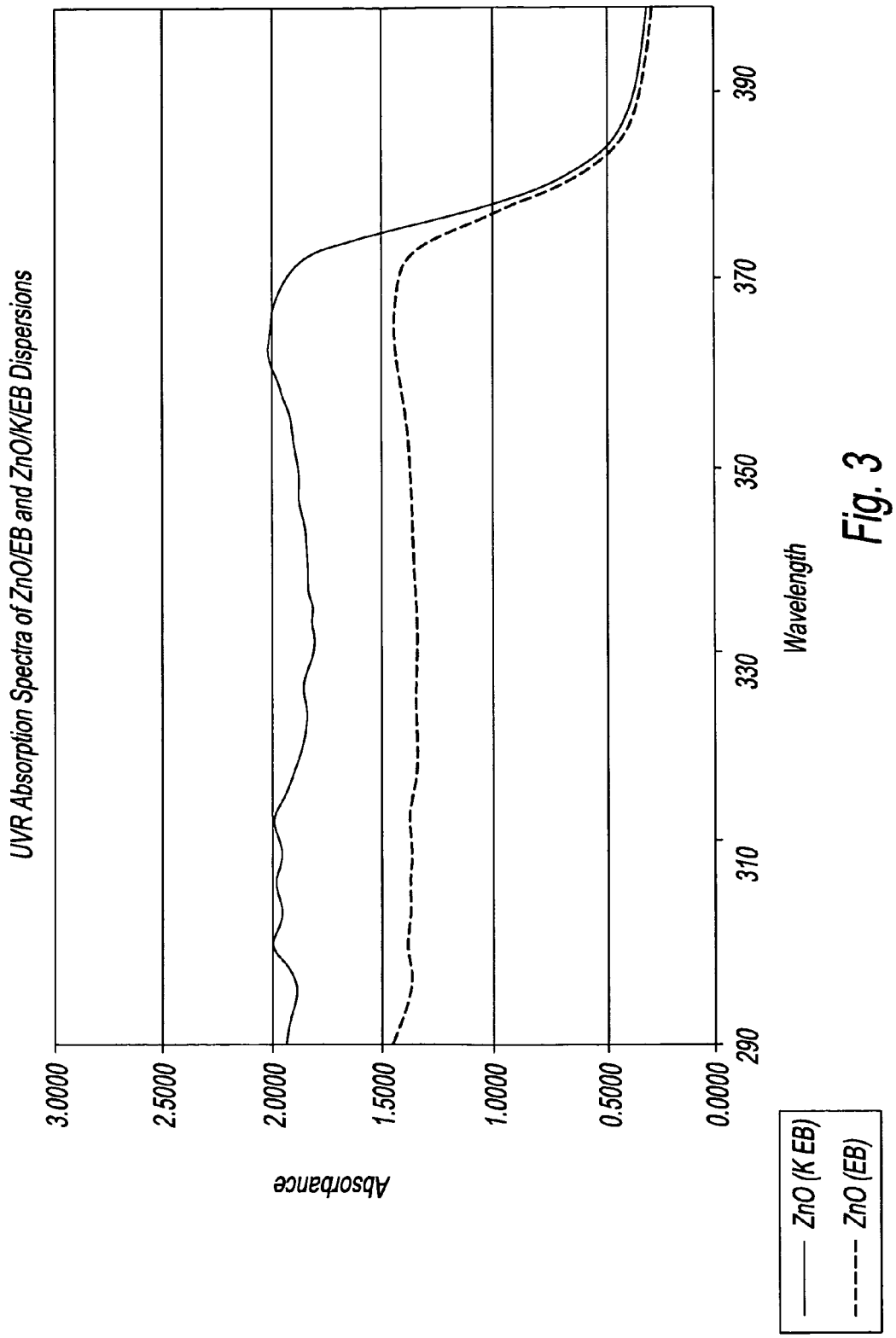
Figure 4:
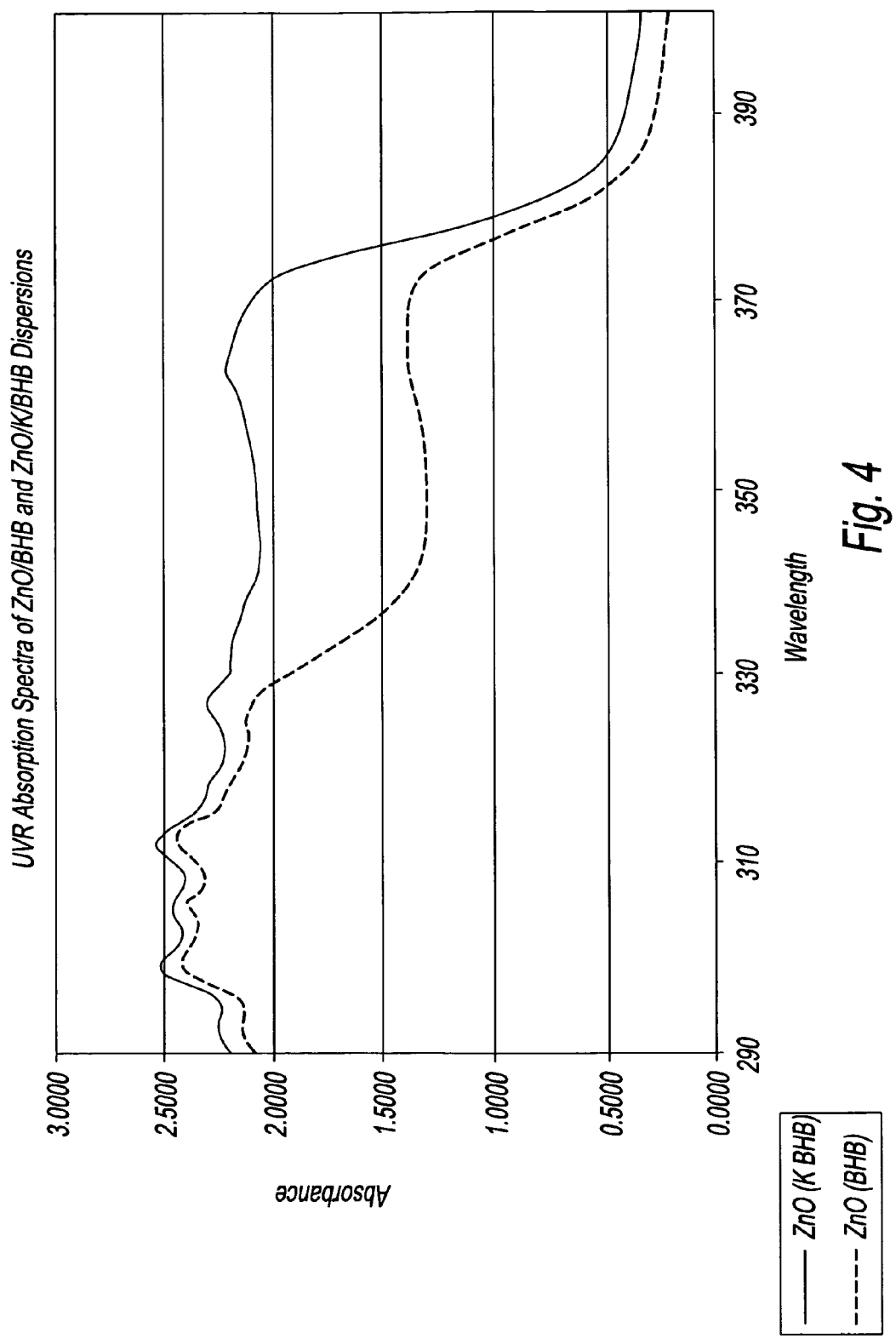

Examples of SPF scans generated by the Labsphere 1000S UV Transmittance Analyzer are shown in FIGS. 2-4. SPF corresponds to absorbance in the UVB region, i.e. approximately 290 nm-320 nm. As shown in FIGS. 2-4, the dispersions of the present disclosure, with both the semiconductor and phenyl compound, exhibit significantly enhanced UVB absorption characteristics over dispersions without the phenyl compounds.

One possible method to confirm the In Vitro SPF results was to compare the dielectric constant of the various dispersions. Solvent polarity can affect the UV absorption spectrum of sunscreen active materials, in that generally increasing polarity enhances sunscreen performance. Therefore, knowledge of solvent polarity, expressed as the dielectric constant, helps to understand simple systems such as the dispersions listed above. It is important to note that factors other than particle size affect the dielectric constant of the ZnO powders. These factors include various crystal lattice defects and unintentional doping. The polarity of several carrier oils of the present disclosure are shown below.

TABLE IV

Solvent Polarity

| Solvent | Dielectric Constant |
|---|---|
| Isopropyl Myristate | 3.25 |
| Isononyl Isonanoate | 3.25 |
| Ethyl hexyl Benzoate | 4.61 |
| Butyloctyl Salicylate | 5.27 |
| Ethylhexyl Salicylate | 6.25 |

For in-vitro SPF testing, the above-described solvents were applied at a dosage rate of 0.233-0.236 mg/cm$^2$ onto PMMA roughened surface plates.

Determining the polarity of a mixture or an emulsion can be performed in various ways. For example, determining a polarity can include measuring a property that is a function of polarity, such as a dielectric constant. Measurement of a dielectric constant of a liquid can be performed by various sensors, such as immersion probes, flow-through probes, and cup-type probes, attached to various meters, such as those available from the Brookhaven Instruments Corporation of Holtsville, N.Y. (e.g., model BI-870) and the Scientifica Company of Princeton, N.J. (e.g. models 850 and 870). For consistency of comparison, preferably all measurements for a particular filter system are performed at substantially the same sample temperature, e.g., by use of a water bath. Generally, the measured dielectric constant of a substance will increase at lower temperatures and decrease at higher temperatures.

Data in Table IV showed that the trend in polarity of the dispersions of the present disclosure as measured by dielectric constant matches the trends observed for SPF, including the small decrease when Kraton is added to the polar solvent. It is remarkable that the addition of ZnO powder with its low dielectric constant of 3.83 should boost the overall dielectric constant of the dispersions. For the dielectric constants of the ZnO/Kraton/solvent dispersions to be of such high magnitude, there has to be a change in dispersion polarity at the molecular (crystalline lattice) level.

TABLE V

Polarity of Dispersions Measured by Dielectric Constant

| | Dielectric Constant | |
|---|---|---|
| Sample | BHB | OS |
| Neat | 5.27 | 6.25 |
| +Kraton | 5.21 | 5.98 |
| +Kraton + ZnO | 8.30 | 10.63 |

ZnO Powder (Undried) Dielectric Constant: 3.83

Figure 5:
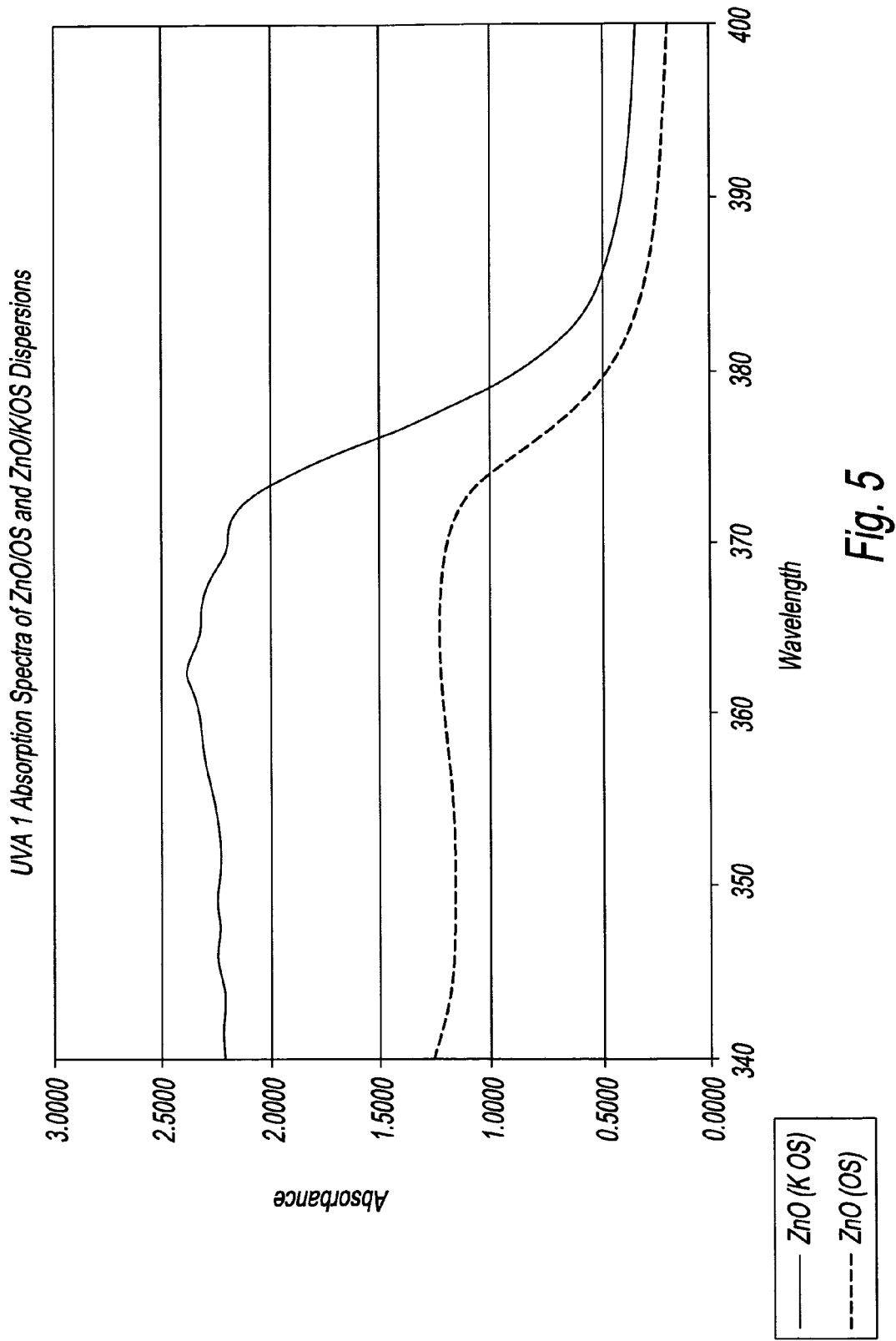
FIGS. 5-7 show the UV absorption data of FIGS. 2-4, respectively, focused on the UVA range.
Figure 6:
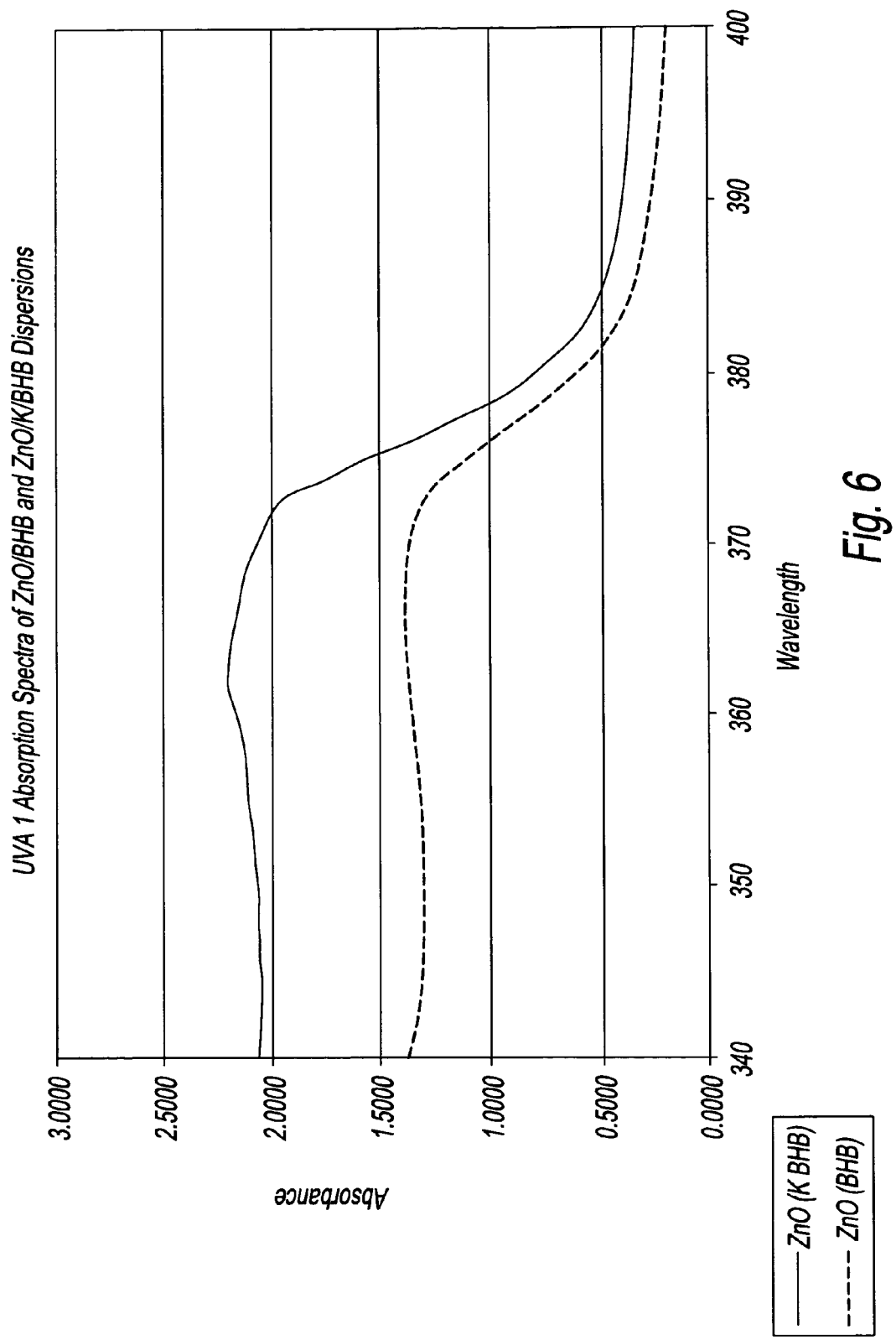
Figure 7:
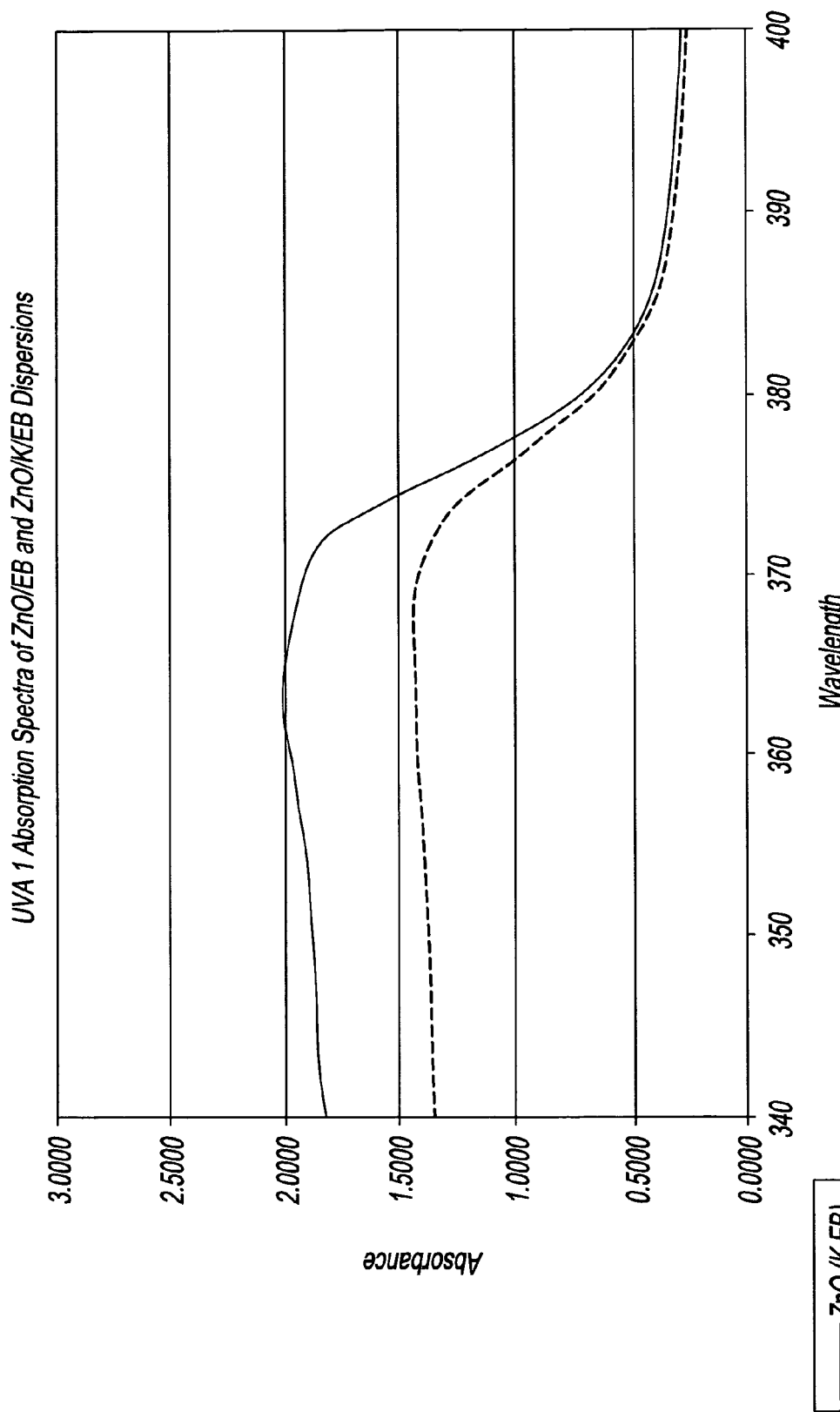
Figure 8:
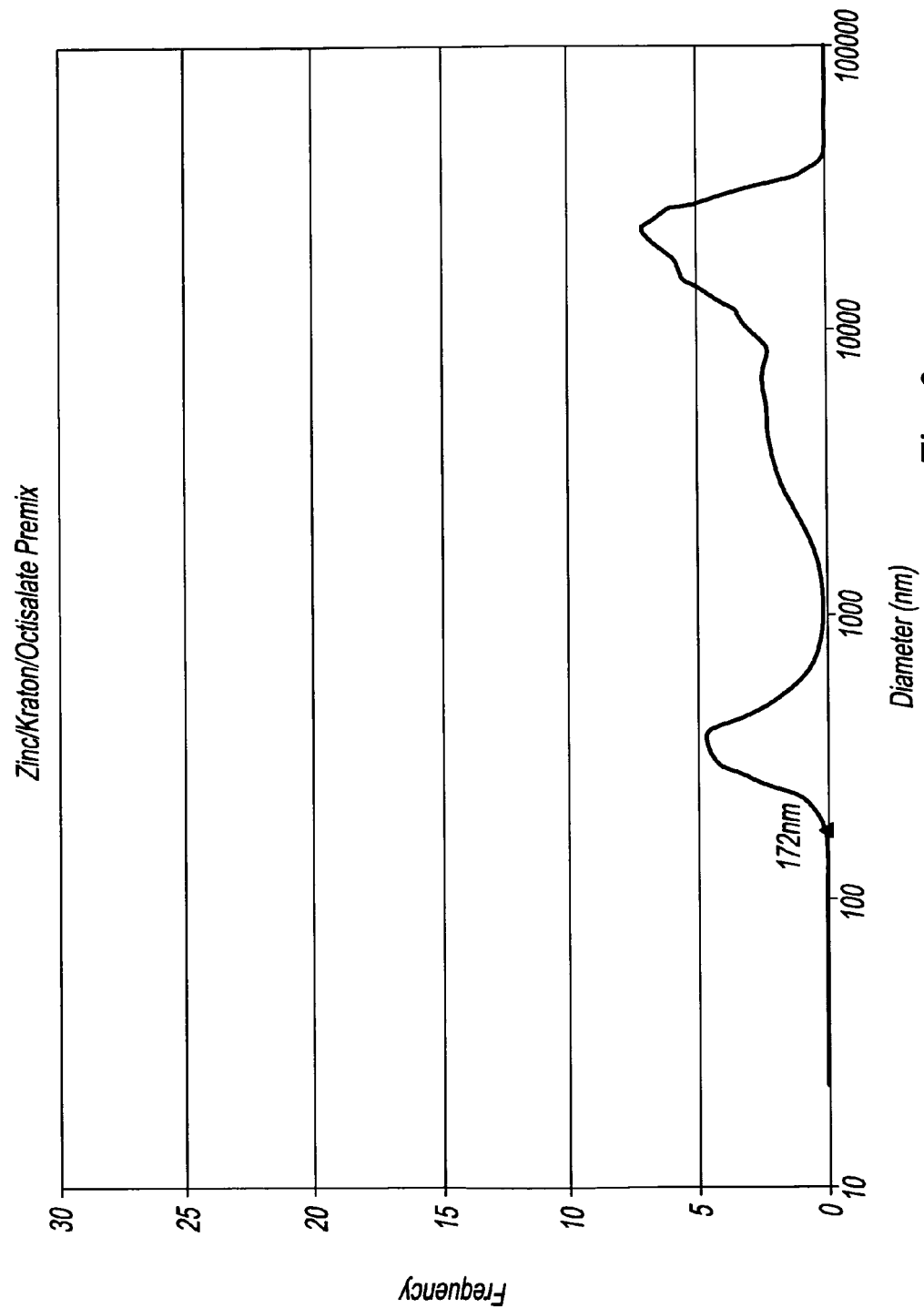
FIGS. 8-11 show graphs illustrating aggregate particle sizes of the semiconductors when in some of the dispersions of the present disclosure.
Figure 9:
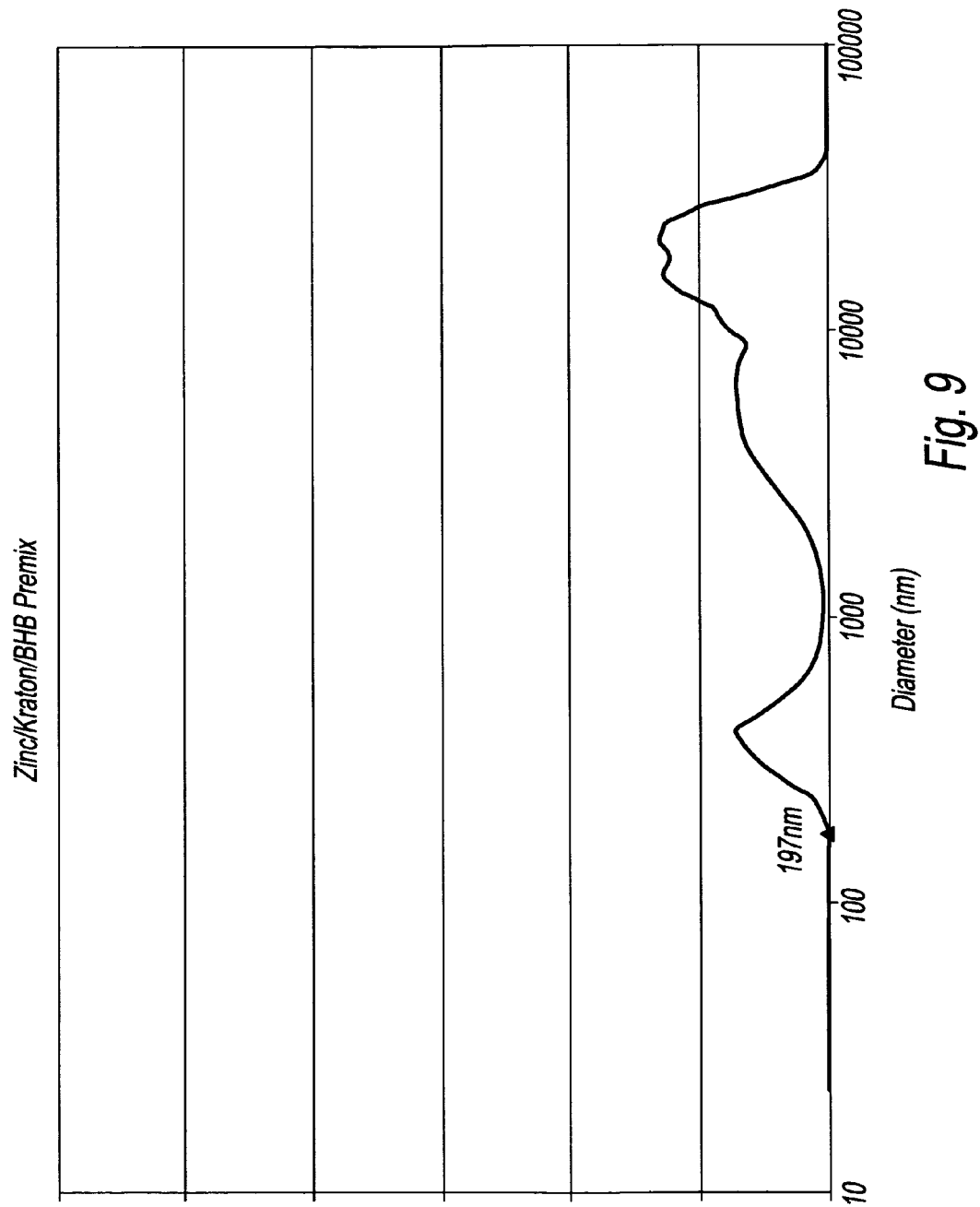
Figure 10:
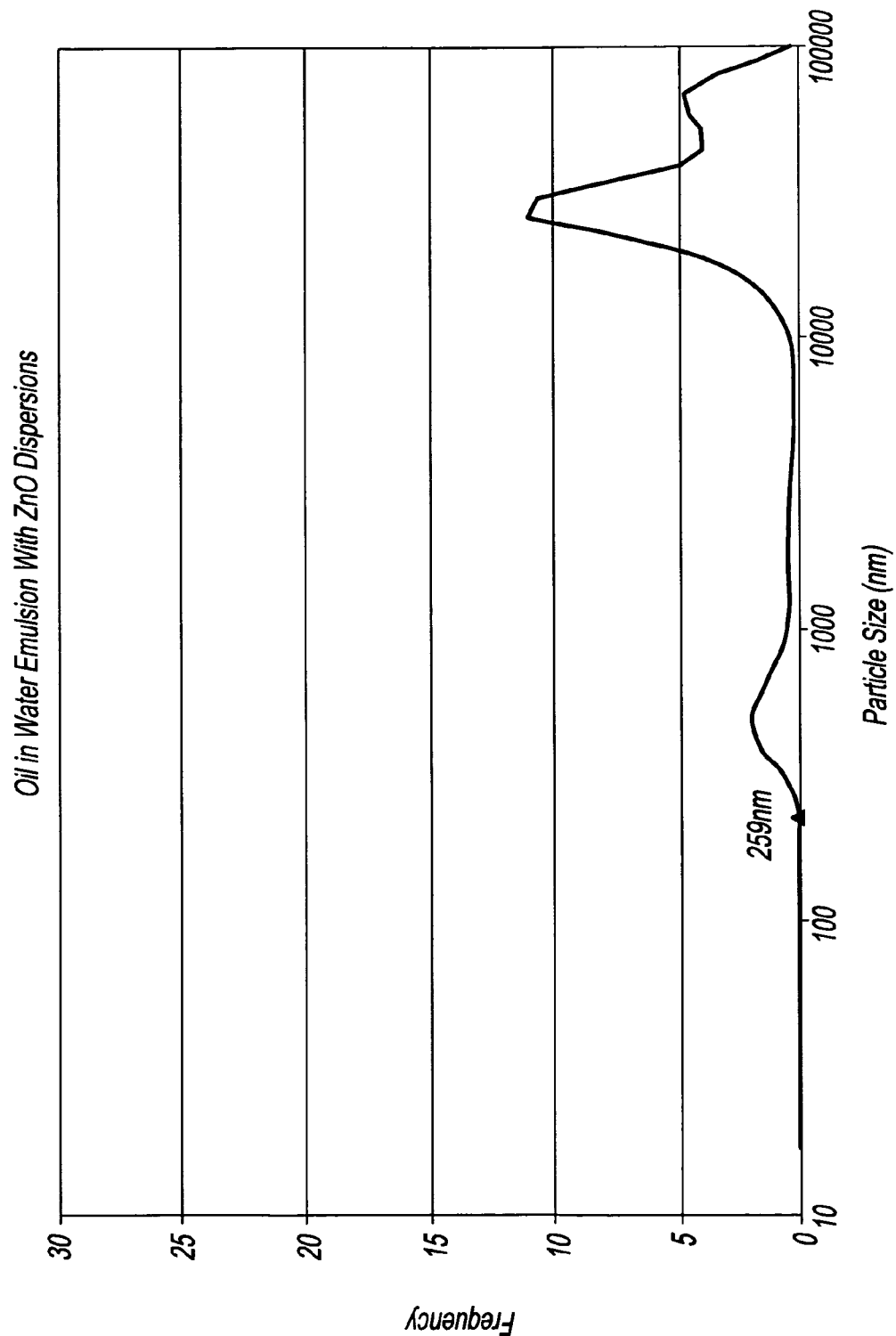
Figure 11:
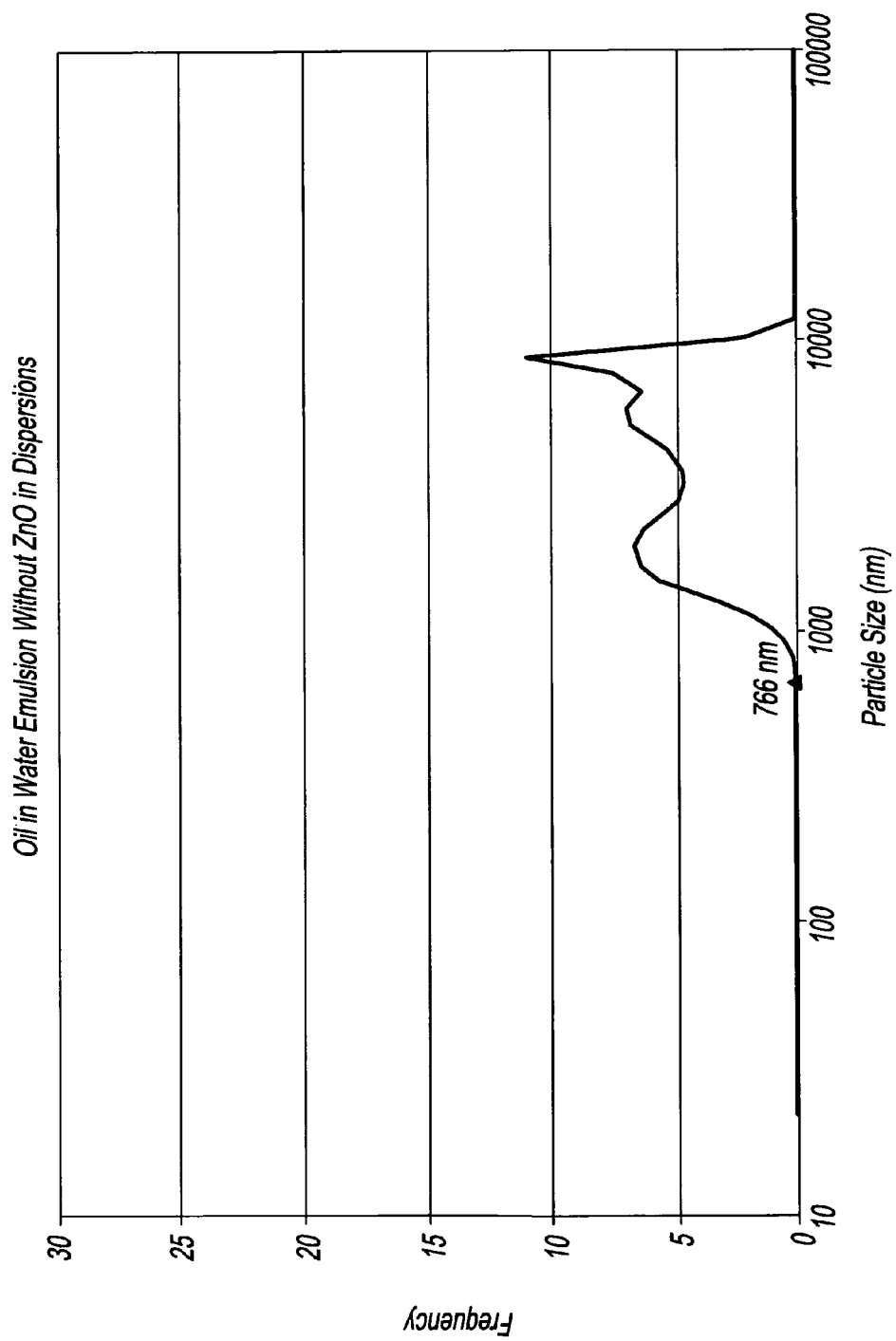

Also, and quite surprisingly, the dispersions of the present disclosure exhibited a significant increase in UVA absorption between 340 nm and 400 nm when comparing dispersions with and without phenyl compounds, as shown in FIGS. 5-7. Obviously, this can be a highly beneficial property of sunscreen compositions. Most notable was the increase in absorption for the UVA1 region of 360-400 nm. A peak appears in the spectra with an approximate initial rise beginning at 360 nm, reaches a maximum that depends on presence of Kraton, and then declines sharply at about 370 nm, and then tails out through 400 nm. The magnitude of the difference in absorption was surprising with values ranging from 38-93% as shown in Table VI. Photoconductivity was definitely enhanced in the overall UVA region, and especially in the UVA1 region.

TABLE VI

Effect of Kraton on Maximum UVA1 Absorbance of ZnO/Solvent

| | EB | | BHB | | OS | |
|---|---|---|---|---|---|---|
| Sample | λnm | Abs. Max | λnm | Abs. Max | λnm | Abs Max |
| ZnO | 366 | 1.46 | 365 | 1.56 | 365 | 1.23 |
| ZnO + Kraton | 362 | 2.02 | 362 | 2.20 | 362 | 2.38 |
| Difference | | 38.4% | | 41.0% | | 93.5% |

In addition to magnitude of absorption in the UVA region, there was a notable and surprising increase in the breadth (red shift) in the absorption band. To characterize the red shift, a fixed absorbance value of 0.5 units was selected and the corresponding wavelength was recorded as shown in Table VII. The data indicated that the influence of Kraton on ZnO caused a red shift in absorbance wavelength thereby expanding the range of absorption efficacy of ZnO in the dispersions. In summary, absorption results in terms of magnitude and breadth in the UVA and UVA1 absorption region support a synergistic enhancement to ZnO photoconductivity.

TABLE VII

Effect of Kraton on Breadth of UVA1 Absorbance of ZnO/Solvent Dispersions

| Sample | λnm for 0.5 Abs EB | λnm for 0.5 Abs BHB | λnm for 0.5 Abs in OS |
|---|---|---|---|
| ZnO | 383.5 | 382.5 | 379.5 |
| ZnO + Kraton | 384.0 | 384.5 | 385.0 |
| Difference | +0.5 | +2.5 | +5.5 |

To further characterize the photoconductivity of the ZnO dispersions, a microwave oven was used as a low energy excitation source. Dielectric heating (also known as electronic heating, RF heating, high-frequency heating) is the phenomenon in which radiowave or microwave electromagnetic radiation heats a dielectric material, especially as caused by dipole rotation. The frequencies used in microwave dielectric heating are 918 MHz and 2450 MHz. Domestic microwave ovens employ 2450 MHz. A Panasonic Microwave Oven 1100 Watt High Power was utilized for these studies. Microwave irradiation induces charged particles to migrate or rotate, which results in polarization of polar particles, and the lag between this polarization and rapid reversals of the microwave field creates friction among molecules to generate heat. In the dispersion systems, the electrons in ZnO and Kraton may vibrate intensely upon absorption of microwaves, and the electrons in the polar solvent may vibrate and rotate intensely, thus generating heat of friction.

The amount of microwave energy absorbed by a given specimen (or "load") depends on many factors. Among these are the size of the load, its orientation with respect to the waves, and the dielectric and thermal properties of the material. Depending upon the material, microwaves may be reflected, passed through, or absorbed. The absorbed microwave energy causes dipolar molecules to rotate (vibrate) at the rate of 2.45 billion cycles per second. The interaction between the rotating dipolar molecules, ions and non-moving molecules induces friction, which in turn produces the heat that warms the solution.

Commercially available ZnO for personal care use has crystal lattice type defects that vary significantly from manufacturer to manufacturer. It is known that ZnO powder alone is transparent to microwave energy for electronic transitions to excited states in the conduction band. However, it is not transparent to vibrational modes of excitation which occur at lower valence band energy levels, and it is not transparent to the magnetic portion of the electromagnetic field.

Experimental conditions for the microwave studies were conducted as routinely as possible to minimize variations among the data sets. Samples were exposed to 30 seconds of microwave energy and temperature immediately recorded with a Type K thermometer. The maximum temperature value was recorded, and the experiment repeated on n=5 new samples for each data set. In these experiments, we decided not to dry the ZnO powder and use it as is because that is the use mode in manufacturing for formulated product. IR results confirmed the presence of water molecules in the ZnO powder. The data summarized in Table Vil indicated that the combination of ZnO/Kraton/Polar Solvent was surprisingly much more effective in absorbing microwave energy than either component alone. The trend in microwave energy absorption among the dispersions followed the trends noted for SPF, UVA, UVA1, and dielectric constant.

TABLE VIII

Absorption of Microwave Energy by ZnO Dispersions

| | Maximum Temperature (° C.) | | |
|---|---|---|---|
| Sample | EB | BHB | OS |
| Solvent Neat | 55.2 ± 1.6 std. dev. | 65.62 ± 1.8 std. dev. | 74.8 ± 1.9 std. dev. |
| Solvent + ZnO + Kraton | 106.4 ± 2.7 std. dev. | 110.02 ± 3.1 std. dev. | 141.4 ± 2.7 std. dev. |

Kraton Powder: 28.4° C. ± 1.5 std. dev.
ZnO Powder (undried): 43.2° C. ± 0.8 std. dev.

The next step involved adding the ZnO/Kraton/BHB and ZnO/Kraton/OS blends to sunscreen formulations for in-vitro and in-vivo testing to help achieve maximum SPF at very water resistant conditions. Although in-vitro SPF was determined using the Labsphere 1000S gave high (unrealistic) values for SPF, it was useful as a relative gauge for formulation development. Formulations were sent to an independent testing facility for in-vivo very water resistant testing according to the method outlined in the Food and Drug Administration (FDA) Monograph for sunscreen testing published in the Federal Register, Vol. 64, No. 98, May 21, 1999, which is incorporated by reference herein.

Prior to this work, several non-ZnO formulations were sent to an independent laboratory for in-vivo SPF very water resistant (VWR) testing. The non-zinc sunscreen formulations were oil-in-water emulsions which included the normally expected additives of emulsifiers, thickeners, stabilizers, film formers, and skin conditioning agents. In several studies, the sunscreen active agents in the formulations included homosalate (10-12%), octisalate (5%), oxybenzone (6%), avobenzone (3%), and octocrylene (6-10%). The in-vivo SPF test results from an independent laboratory were quite surprising in that lower amounts of organic sunscreen agents were used in conjunction with the ZnO dispersions to achieve significantly higher SPF and PFA results as shown in Table IX.

TABLE IX

Evaluation of Sunscreen Lotion Containing ZnO/K/Polar Solvent Dispersions

| Sunscreen Actives | Avobenzone 3.0% Homosalate 10.0% Octocrylene 6.0% | Octisalate 5.0% Oxybenzone 6.0% Zinc Oxide 3.0% |
|---|---|---|
| In Vivo Test | Method | Result |
| SPF Static | FDA Monograph, 3 Subjects, UVB Efficacy | 115 ± 5 SPF units |
| SPF VWR | FDA Monograph, 20 Subjects, UVB Efficacy | 102.63 average 100.33 @ 95% C.L. |
| PFA | JCIA Method, 10 Subjects, UVA Efficacy | 45.58 average 40.87 @ 95% C.L. |

Another indicator of performance is sunscreen efficiency, which is a ratio of SPF units to amount of sunscreen active. Commercially available product with somewhat similar levels of organic sunscreen actives and no metal oxide sunscreen actives generally have an SPF VWR rating of 80-85, yielding a sunscreen efficiency of 2.4-2.5:1. These non-zinc products contain homosalate levels at 12-15%. Sunscreen efficiency in the sunscreen compositions of the present disclosure, which contain a combination of organic UV filters and unique zinc oxide dispersions, was an impressive 3.0:1. The SPF VWR 100 sunscreen formulation containing ZnO is the only combination product with organic sunscreen filters and metal oxide achieving having remarkable and surprisingly high SPF at water resistant test conditions and broadest spectrum UVR absorption. This sunscreen efficiency ratio demonstrated the "end product" performance value and of having enhanced photoconductivity of semiconductors.

One other advantage of the zinc oxide dispersions is that the system allows the zinc oxide crystals to remain as aggregates with particle sizes greater than 100 microns. This is significant because of concerns raised about nano-sized particles. Results from particle size analyses using a Horiba LA-920 indicated that there are no nanoparticles present in the dispersions or finished formulation. A comparison of FIGS. 8-11 indicated the presence of a peak associated with ZnO when comparing samples of ZnO to the control sample which is the oil-in-water emulsion without ZnO present. The very first particle size recorded for each sample is presented in Table X.

TABLE X

Smallest Particle Size Detected

| Sample | Particle Size (nm) |
|---|---|
| ZnO/Kraton/BHB Dispersion | 197 |
| ZnO/Kraton/OS Dispersion | 172 |
| O/W Emulsion with ZnO Dispersions | 259 |
| O/W Emulsion without ZnO, with Kraton/Solvents | 766 |

The present invention having been thus described with particular reference to the preferred forms thereof, it will be obvious that various changes and modifications may be made therein without departing from the spirit and scope of the present invention as defined in the appended claims.

What is claimed is:

1. A sunscreen composition, comprising:
   (i) a dispersion, wherein said dispersion comprises:
      a. about 1.00 wt. % to about 5.00 wt. %, based on the total weight of the sunscreen composition, of a semiconductor sunscreen active comprising zinc oxide;
      b. a compound having multiple phenyl groups comprising ethylene/butadiene/styrene block copolymer; and
      c. a polar carrier oil selected from the group consisting of isopropyl myristate, butyloctyl salicylate, octisalate, isononyl isonanoate, and ethylhexyl benzoate, and any combinations thereof; and
   (ii) about 3 wt. % to about 12 wt. %, based on the total weight of the composition, of an additional sunscreen active selected from the group consisting of cinnamate, homosalate, octisalate, oxybenzone, avobenzone, and octocrylene, and any combinations thereof,
wherein said sunscreen composition has a sunscreen efficiency ratio of at least 3.0:1.

2. The sunscreen composition of claim 1, wherein said compound with multiple phenyl groups is present in an amount of about 0.05 wt. % to about 10.00 wt. %, based on the total weight of the dispersion.

3. The sunscreen composition of claim 2, wherein said compound with multiple phenyl groups is present in an amount of about 0.10 wt. % to about 5 wt. %, based on the total weight of the dispersion.

4. The sunscreen composition of claim 1, wherein said polar carrier oil is present in an amount of about 65.00 wt. % to about 99.50 wt. %, based on the total weight of the dispersion.

5. The sunscreen composition of claim 1, wherein said polar carrier oil is present in an amount of about 75.00 wt. % to about 95.00 wt. %, based on the total weight of the dispersion.

6. The sunscreen composition of claim 1, further comprising one or more additives selected from the group consisting of emulsifiers, thickeners, emollients, pH adjusters, stabilizers, and film formers.

7. The sunscreen composition of claim 1, wherein the minimum aggregate particle size of said semiconductor is 100 microns.

8. The sunscreen composition of claim 1, wherein said phenyl compound is present in an amount of about 5 wt. % to about 10 wt. %, based on the total weight of the dispersion.

9. A sunscreen composition, comprising:
   (i) a dispersion, wherein said dispersion comprises:
      a. a semiconductor sunscreen active comprising zinc oxide;
      b. a compound having multiple phenyl groups comprising ethylene/butadiene/styrene block copolymer; and
      c. a polar carrier oil selected from the group consisting of isopropyl myristate, butyloctyl salicylate, octisalate, isononyl isonanoate, and ethylhexyl benzoate, and any combinations thereof; and
   (ii) about 3 wt. % to about 12 wt. %, based on the total weight of the composition, of an additional sunscreen active selected from the group consisting of cinnamate, homosalate, octisalate, oxybenzone, avobenzone, and octocrylene, and any combinations thereof,
wherein said sunscreen composition has a sunscreen efficiency ratio of at least 3.0:1.

10. The sunscreen composition of claim 9, wherein the minimum aggregate particle size of said semiconductor is 100 microns.

11. The sunscreen composition of claim 9, wherein the amount of semiconductor sunscreen active is present in an amount of about 20 wt. % to about 30 wt. % based on the total weight of the dispersion.

12. The sunscreen composition of claim 11, wherein the amount of the compound having multiple phenyl groups is present in an amount of about 0.05 wt. % to about 10 wt. %, based on the total weight of the dispersion.

13. The sunscreen composition of claim 12, wherein the amount of polar carrier oil is present in an amount of about 65 wt. % to about 95 wt. %, based on the total weight of the dispersion.

14. The sunscreen composition of claim 9, wherein the dispersion includes a matrix with an electromagnetic cloud, and wherein the semiconductor is distributed throughout the matrix.

* * * * *